United States Patent
Sawant et al.

(10) Patent No.: US 9,227,958 B2
(45) Date of Patent: Jan. 5, 2016

(54) AMORPHOUS AND CRYSTALLINE FORMS OF APREPITANT AND PROCESSES FOR THE PREPARATION THEREOF

(75) Inventors: Mangesh Shivram Sawant, Mumbai (IN); Girish Dixit, Navi Mumbai (IN); Nitin Sharad Chandra Pradhan, Thane (IN); Mubeen Ahmad Khan, Navi Mumbai (IN); Sukumar Sinha, Navi Mumbai (IN)

(73) Assignee: Glenmark Pharmaceuticals Limited, Mumbai (IN)

(*) Notice: Subject to any disclaimer, the term of this patent is extended or adjusted under 35 U.S.C. 154(b) by 2011 days.

(21) Appl. No.: 12/223,514

(22) PCT Filed: Feb. 2, 2007

(86) PCT No.: PCT/IB2007/000269
§ 371 (c)(1),
(2), (4) Date: Sep. 22, 2008

(87) PCT Pub. No.: WO2007/088483
PCT Pub. Date: Aug. 9, 2007

(65) Prior Publication Data
US 2009/0192161 A1    Jul. 30, 2009

Related U.S. Application Data

(60) Provisional application No. 60/782,765, filed on Mar. 16, 2006.

(30) Foreign Application Priority Data

Feb. 3, 2006  (IN) ............................ 168/MUM/2006
Feb. 7, 2006  (IN) ............................ 184/MUM/2006
Mar. 10, 2006 (IN) ............................ 353/MUM/2006

(51) Int. Cl.
*A61K 31/5377* (2006.01)
*C07D 413/06* (2006.01)
(Continued)

(52) U.S. Cl.
CPC .................................. *C07D 413/06* (2013.01)

(58) Field of Classification Search
CPC ..................................................... C07D 413/06
USPC ................. 424/400; 514/235.2, 241; 544/132
See application file for complete search history.

(56) References Cited

U.S. PATENT DOCUMENTS 5,691,336 A   11/1997   Dorn et al.
5,719,147 A    2/1998   Dorn et al.
(Continued)

FOREIGN PATENT DOCUMENTS

WO    WO-9516679      6/1995
WO    WO 9516679  *   6/1995
(Continued)

OTHER PUBLICATIONS

Keck, Cornelia M. & Müller, Rainer H. "Drug nanocrystals of poorly soluble drugs produced by high pressure homogenisation", European Journal of Pharmaceutics and Biopharmaceutics (2006, available online Aug. 29, 2005) 62: 3-16.*
(Continued)

*Primary Examiner* — Ernst V Arnold
*Assistant Examiner* — Hong Yu
(74) *Attorney, Agent, or Firm* — Blank Rome LLP (57) ABSTRACT

An amorphous form of aprepitant and a process for its preparation is provided. Also provided are mixtures of polymorph Forms I and II of aprepitant and a process for the preparation thereof.

13 Claims, 7 Drawing Sheets

(51) Int. Cl.
  *A61P 1/08* (2006.01)
  *A61K 31/53* (2006.01)
  *C07D 417/06* (2006.01)

(56) References Cited

U.S. PATENT DOCUMENTS

| | | | |
|---|---|---|---|
| 6,096,742 | A | 8/2000 | Crocker et al. |
| 6,229,010 | B1 * | 5/2001 | Crocker et al. ............... 544/132 |
| 8,217,039 | B2 * | 7/2012 | Mathad et al. ................ 514/241 |
| 2004/0214746 | A1 * | 10/2004 | Bosch et al. ..................... 514/1 |
| 2008/0214535 | A1 * | 9/2008 | Mathad et al. ............. 514/230.8 |

FOREIGN PATENT DOCUMENTS

| | | |
|---|---|---|
| WO | WO 99/01444 | 1/1999 |
| WO | WO 99/65900 | 12/1999 |
| WO | WO 03/049718 | 6/2003 |
| WO | WO 03/089429 | 10/2003 |

OTHER PUBLICATIONS

Zhang et al., "Phase transformation consideration during process development and manufacture of solid oral dosage forms", Advanced Drug Delivery Reviews, 56, 371-390 (2004).*

Gilbert S. Banker et al., "Morden Pharmaceutics", Marcel Deckker, Inc., 2002, p. 156.*

Helmy et al., "Characterization and Quantitation of Aprepitant Drug Substance Polymorphs by Attenuated Total Reflectance Fourier Transform Infrared Spectrocopy" *Analytical Chemistry*, vol. 75, No. 3, Feb. 2003, pp. 605-611.

Dec. 15, 1998 Preliminary Amendment filed in U.S. Appl. No. 09/212,511 (now U.S. Pat. No. 6,096,742).

Glenmark Opposition 3 dated Jun. 3, 2014 in Interference No. 105,927.

Sep. 18, 2014 Decision on Priority in Interference No. 105,927.

* cited by examiner

AMORPHOUS AND CRYSTALLINE FORMS OF APREPITANT AND PROCESSES FOR THE PREPARATION THEREOF

PRIORITY

This application claims priority under 35 U.S.C. §371 to International Application No. PCT/IB2007/000269, filed Feb. 2, 2007 [and entitled "AMORPHOUS AND CRYSTALLINE FORMS OF APREPITANT AND PROCESSES FOR THE PREPARATION THEREOF",] which claims priority to Indian Provisional Application No. 353/MUM/2006, filed on Mar. 10, 2006[, and entitled "POLYMORPHIC FORMS FO APREPITANT AND PROCESS FOR THE PREPARATION THEREOF",] and to U.S. Provisional Application No. 60/782,765, filed on Mar. 16, 2006[, and entitled "PROCESS FOR THE PREPARATION OF AMORPHOUS APREPITANT"] and to Indian Provisional Application No. 184/MUM/2006, filed on Feb. 3, 2006[, and entitled "AMORPHOUS APREPITANT AND PROCESS FOR THE PREPITATION THEREOF"], the contents of each of which are incorporated by reference herein.

BACKGROUND OF THE INVENTION

1. Technical Field

The present invention generally relates to amorphous and crystalline forms of aprepitant and processes for their preparation.

2. Description of Related Art

Aprepitant, also known as 5-[[(2R,3S)-2-[(1R-1-[3,5-bis(trifluoromethyl)phenyl]ethoxy]-3-(4-fluorophenyl)-4-morpholinyl]methyl]-1,2-dihydro-3H-1,2,4-triazol-3-one, is represented by the structure of Formula I:

Aprepitant is a selective high-affinity antagonist of human substance P/neurokinin 1 ($NK_1$) receptors. Aprepitant has little or no affinity for serotonin (5-HT3), dopamine and corticosteroid receptors, which are the targets of some therapies for chemotherapy-induced nausea and vomiting (CINV). Aprepitant, in combination with other antiemetic agents, is indicated for the prevention of acute and delayed nausea and vomiting associated with initial and repeat courses of highly emetogenic cancer chemotherapy, including high-dose cisplatin and is commercially sold under the trade name Emend®. See, e.g., Physician's Desk Reference, "Emend," 60th Edition, pp. 1944-1949 (2005).

U.S. Pat. No. 5,719,147 discloses aprepitant and a process for its preparation.

U.S. Pat. No. 6,096,742 discloses a polymorphic form of the compound 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methylmorpholine characterized by an X-ray powder diffraction pattern with key reflections at approximately: 12.0, 15.3, 16.6, 17.0, 17.6, 19.4, 20.0, 21.9, 23.6, 23.8, and 24.8.degree. (2 theta) which is substantially free of a polymorphic form of the compound 2-(R)-(1-(R)-(3,5-bis(trifluoromethyl)phenyl)ethoxy)-3-S)-(4-fluoro)-phenyl-4-(3-(5-oxo-1H,4H-1,2,4-triazolo)methylmorpholine characterized by an X-ray powder diffraction pattern with key reflections at approximately: 12.6, 16.7, 17.1, 17.2, 18.0, 20.1, 20.6, 21.1, 22.8, 23.9, and 24.8.degree. (2 theta).

The present invention relates to the solid state physical properties of aprepitant. These properties can be influenced by controlling the conditions under which aprepitant is obtained in solid form. Solid state physical properties affect the ease with which the material is handled during processing into a pharmaceutical product such as a tablet or capsule formulation. The physical properties can also impact the type of excipients, for instance, to add to an aprepitant formulation. Furthermore, the solid state physical property of a pharmaceutical compound is important to its dissolution in aqueous fluid or even in a patient's stomach fluid, which have therapeutic consequences. The rate of dissolution is also a consideration in liquid forms of medicine as well. The solid state form of a compound may also affect its storage conditions.

These practical physical characteristics are influenced by the particular form of a substance. For example, polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predicable solubility profiles. The amorphous and crystalline forms of a compound can be distinguished in a laboratory by X-ray diffraction spectroscopy and by other methods such as, infrared spectrometry.

Generally, amorphous materials do not exhibit the three dimensional long-range order ordinarily found in crystalline material and are structurally more similar to liquids where the arrangement of molecules is random. Additionally, amorphous solids are substantially not crystalline and therefore do not give a definitive x-ray diffraction pattern (XPD). They also do not give rise to a melting point and tend to liquefy at some point beyond the glass transition point.

The present invention relates to an amorphous form and polymorphic mixtures of aprepitant. Moreover the present invention relates to additional processes for preparation of amorphous aprepitant and polymorphic mixtures of aprepitant.

SUMMARY OF THE INVENTION

In accordance with one embodiment, the present invention provides an amorphous form of aprepitant.

In accordance with a second embodiment of the present invention, a pharmaceutical composition is provided comprising a therapeutically effective amount of an amorphous form of aprepitant.

In accordance with third embodiment of the present invention, a process for the preparation of aprepitant in an amorphous form is provided comprising (a) providing a solution comprising aprepitant in one or more solvents capable of dissolving the aprepitant; and (b) substantially removing the solvent from the solution to provide amorphous aprepitant.

In accordance with a fourth embodiment of the present invention, a polymorphic mixture is provided comprising at least about 5 weight %, based on the total weight of the mixture, of polymorph Form I or polymorph Form II of aprepitant, with the remaining amount of the mixture being the other polymorph form of aprepitant.

In accordance with a fifth embodiment of the present invention, a polymorphic mixture is provided comprising about 5 weight % to about 75 weight % of polymorph Form I of aprepitant and about 95 weight % to about 25 weight % of polymorph Form II of aprepitant.

In accordance with a sixth embodiment of the present invention, a polymorphic mixture is provided comprising about 11 weight % (±5%) of polymorph Form I of aprepitant and about 89 weight % (±5%) of polymorph Form II of aprepitant.

In accordance with a seventh embodiment of the present invention, a polymorphic mixture is provided comprising about 20 weight % (+5%) of polymorph Form I of aprepitant and about 80 weight % (+5%) of polymorph Form II of aprepitant.

In accordance with an eighth embodiment of the present invention, a polymorphic mixture is provided comprising about 30 weight % (+5%) of polymorph Form I of aprepitant and about 70 weight % (+5%) of polymorph Form II of aprepitant.

In accordance with a ninth embodiment of the present invention, a polymorphic mixture is provided comprising about 65 weight % (+5%) of polymorph Form I of aprepitant and about 35 weight % (+5%) of polymorph Form II of aprepitant.

In accordance with a tenth embodiment of the present invention, a pharmaceutical composition is provided comprising a therapeutically effective amount of a polymorphic mixture comprising at least about 5 weight % of polymorph Form I or polymorph Form II of aprepitant, with the remaining amount of the mixture being the other polymorph form of aprepitant.

In accordance with an eleventh embodiment of the present invention, a pharmaceutical composition is provided comprising a therapeutically effective amount of a polymorphic mixture comprising about 5 weight % to about 75 weight % of polymorph Form I of aprepitant and about 95 weight % to about 25 weight % polymorph Form II of aprepitant.

In accordance with a twelfth embodiment of the present invention, a pharmaceutical composition is provided comprising a therapeutically effective amount of a polymorphic mixture comprising about 11 weight % (+5%) of polymorph Form I of aprepitant and about 89 weight % (+5%) of polymorph Form II of aprepitant.

In accordance with a thirteenth embodiment of the present invention, a pharmaceutical composition is provided comprising a therapeutically effective amount of a polymorphic mixture comprising about 20 weight % (+5%) of polymorph Form I of aprepitant and about 80 weight % (+5%) of polymorph Form II of aprepitant.

In accordance with a fourteenth embodiment of the present invention, a pharmaceutical composition is provided comprising a therapeutically effective amount of a polymorphic mixture comprising about 30 weight % (+5%) of polymorph Form I of aprepitant and about 70 weight % (+5%) of polymorph Form II of aprepitant.

In accordance with a fifteenth embodiment of the present invention, a pharmaceutical composition is provided comprising a therapeutically effective amount of a polymorphic mixture comprising about 65 weight % (+5%) of polymorph Form I of aprepitant and about 35 weight % (+5%) of polymorph Form II of aprepitant.

In accordance with a sixteenth embodiment of the present invention, a method is provided comprising administering to a subject at least one of the foregoing pharmaceutical compositions.

In accordance with a seventeenth embodiment of the present invention, a method of treatment is provided comprising administering to a subject at least one of the foregoing pharmaceutical compositions.

DEFINITIONS

The term "treating" or "treatment" of a state, disorder or condition as used herein means: (1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms. The benefit to a subject to be treated is either statistically significant or at least perceptible to the patient or to the physician.

The term "therapeutically effective amount" as used herein means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The term "delivering" as used herein means providing a therapeutically effective amount of an active ingredient to a particular location within a host means causing a therapeutically effective blood concentration of the active ingredient at the particular location. This can be accomplished, e.g., by topical, local or by systemic administration of the active ingredient to the host.

The term "subject" or "patient" or "host" as used herein refers to mammalian animals, preferably human.

The term "buffering agent" as used herein is intended to mean a compound used to resist a change in pH upon dilution or addition of acid of alkali. Such compounds include, by way of example and without limitation, potassium metaphosphate, potassium phosphate, monobasic sodium acetate and sodium citrate anhydrous and dehydrate and other such material known to those of ordinary skill in the art.

The term "sweetening agent" as used herein is intended to mean a compound used to impart sweetness to a preparation. Such compounds include, by way of example and without limitation, aspartame, dextrose, glycerin, mannitol, saccharin sodium, sorbitol, sucrose, fructose and other such materials known to those of ordinary skill in the art.

The term "binders" as used herein is intended to mean substances used to cause adhesion of powder particles in tablet granulations. Such compounds include, by way of example and without limitation, acacia alginic acid, tragacanth, carboxymethylcellulose sodium, polyvinylpyrrolidone, compressible sugar (e.g., NuTab), ethylcellulose, gelatin, liquid glucose, methylcellulose, povidone and pregelatinized starch, combinations thereof and other material known to those of ordinary skill in the art.

When needed, other binders may also be included in the present invention. Exemplary binders include starch, poly (ethylene glycol), guar gum, polysaccharide, bentonites, sugars, invert sugars, poloxamers (PLURONIC™ F68, PLURONIC™ F127), collagen, albumin, celluloses in nonaqueous solvents, combinations thereof and the like. Other binders include, for example, poly(propylene glycol), polyoxyethylene-polypropylene copolymer, polyethylene ester, polyethylene sorbitan ester, poly(ethylene oxide), microcrystalline cellulose, poly(vinylpyrrolidone), combinations thereof and other such materials known to those of ordinary skill in the art.

The term "diluent" or "filler" as used herein is intended to mean inert substances used as fillers to create the desired bulk, flow properties, and compression characteristics in the preparation of tablets and capsules. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

The term "glidant" as used herein is intended to mean agents used in tablet and capsule formulations to improve flow-properties during tablet compression and to produce an anti-caking effect. Such compounds include, by way of example and without limitation, colloidal silica, calcium silicate, magnesium silicate, silicon hydrogel, corn starch, talc, combinations thereof and other such materials known to those of ordinary skill in the art.

The term "lubricant" as used herein is intended to mean substances used in tablet formulations to reduce friction during tablet compression. Such compounds include, by way of example and without limitation, calcium stearate, magnesium stearate, mineral oil, stearic acid, zinc stearate, combinations thereof and other such materials known to those of ordinary skill in the art.

The term "disintegrant" as used herein is intended to mean a compound used in solid dosage forms to promote the disruption of the solid mass into smaller particles which are more readily dispersed or dissolved. Exemplary disintegrants include, by way of example and without limitation, starches such as corn starch, potato starch, pregelatinized and modified starched thereof, sweeteners, clays, such as bentonite, microcrystalline cellulose (e.g. Avicel™), carsium (e.g. Amberlite™), alginates, sodium starch glycolate, gums such as agar, guar, locust bean, karaya, pectin, tragacanth, combinations thereof and other such materials known to those of ordinary skill in the art.

The term "wetting agent" as used herein is intended to mean a compound used to aid in attaining intimate contact between solid particles and liquids. Exemplary wetting agents include, by way of example and without limitation, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, (e.g., TWEEN™s), polyethylene glycols, polyoxyethylene stearates colloidal silicon dioxide, phosphates, sodium dodecylsulfate, carboxymethylcellulose calcium, carboxymethylcellulose sodium, methylcellulose, hydroxyethylcellulose, hydroxylpropylcellulose, hydroxypropylmethylcellulose phthalate, noncrystalline cellulose, magnesium aluminum silicate, triethanolamine, polyvinyl alcohol, polyvinylpyrrolidone (PVP), tyloxapol (a nonionic liquid polymer of the alkyl aryl polyether alcohol type, also known as superinone or triton), combinations thereof and other such materials known to those of ordinary skill in the art.

Most of these excipients are described in detail in, e.g., Howard C. Ansel et al., Pharmaceutical Dosage Forms and Drug Delivery Systems, (7th Ed. 1999); Alfonso R. Gennaro et al., Remington: The Science and Practice of Pharmacy, (20th Ed. 2000); and A. Kibbe, Handbook of Pharmaceutical Excipients, (3rd Ed. 2000), which are incorporated by reference herein.

DETAILED DESCRIPTION OF THE PREFERRED EMBODIMENTS

Figure 1:
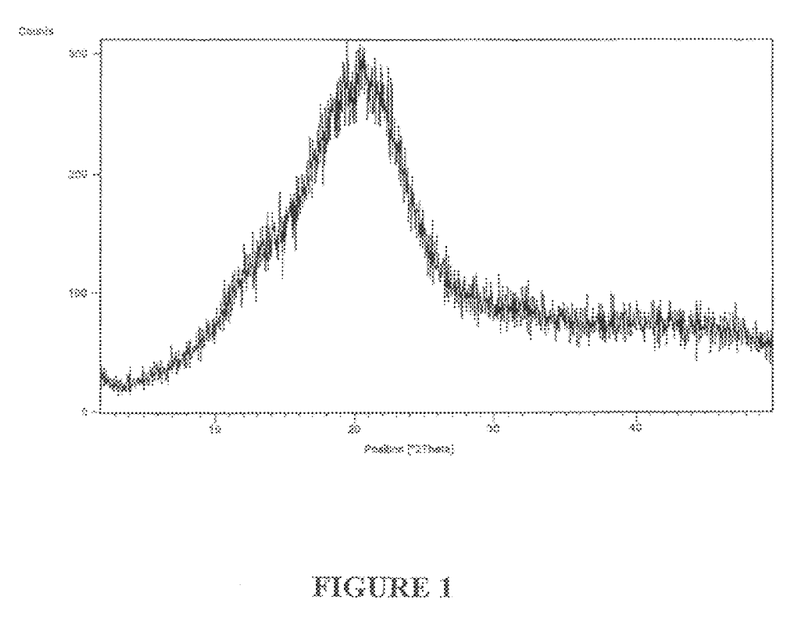
FIG. 1 is a characteristic powder x-ray diffraction (XRD) pattern of amorphous aprepitant.
Figure 2:
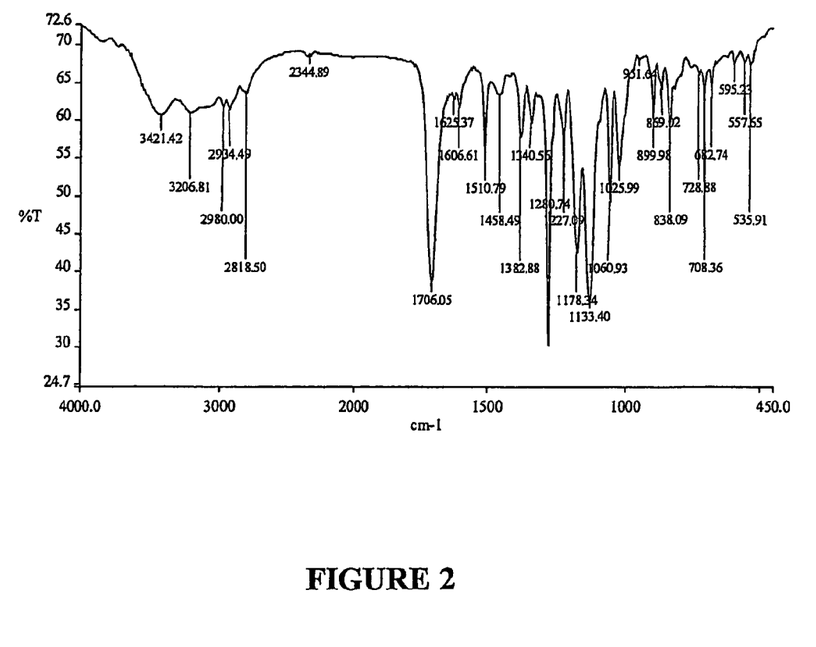
FIG. 2 is an infrared (IR) spectrum pattern of amorphous aprepitant.

One embodiment of the present invention provides amorphous aprepitant. In another embodiment, the present invention provides aprepitant in a solid form, wherein at least 80% by weight of the solid aprepitant is an amorphous form of aprepitant. Another embodiment provides aprepitant substantially in amorphous form. Substantially amorphous aprepitant can contain a very low content of crystalline amorphous aprepitant, e.g., less than about 5% crystallinity, preferably less than about 2%, and preferably less than about 1% crystallinity. Crystallinity may be measured using methods familiar to those skilled in the art. These methods include, but are not limited to powder X-ray diffraction, differential scanning calorimetry, dynamic vapor sorption, isothermal microcalorimetry, inverse gas chromatography, near infra-red spectroscopy and solid-state NMR. The amorphous aprepitant of the present invention is in substantially pure form. The substantially pure form of amorphous aprepitant can have a chemical purity of equal to or greater than about 98% as measured by HPLC, preferably equal to or greater than about 99%, and most preferably equal to or greater than about 99.5%. The XRD and IR patterns of amorphous aprepitant of the present invention are substantially in accordance with FIGS. 1 and 2.

The amorphous aprepitant of the present invention can be obtained by at least (a) providing a solution comprising aprepitant in one or more solvents capable of dissolving the aprepitant; and (b) substantially removing the solvent from the solution to provide amorphous aprepitant.

In step (a) of the process of the present invention a solution is formed containing at least aprepitant and a solvent capable of dissolving the aprepitant. The aprepitant used as a starting material in the process can be in any form, e.g., hydrates, solvates, polymorphic forms of aprepitant and the like. Methods for preparing aprepitant are well known, see, e.g., U.S. Pat. Nos. 5,719,147 and 6,096,742. Suitable solvents capable of dissolving aprepitant for use herein include, but are not limited to, alcoholic solvents having from 1 to 6 carbon atoms, aromatic hydrocarbon solvents, non-aromatic hydrocarbon solvents, water, and the like and mixtures thereof. Useful alcoholic solvents include, but are not limited to, methanol, ethanol, propanol, and the like and mixtures thereof. Useful aromatic hydrocarbon solvents include, but are not limited to, benzene, toluene, xylene and the like and mixtures thereof. Useful non-aromatic hydrocarbon solvents include, but are not limited to, hexane, heptane and the like and mixtures thereof. Preferably, the solvent is an alcohol or a mixture of an alcohol with water, and most preferably a mixture of methanol and water. The amount of solvent can range from about 10 to about 35% w/v and preferably from about 15 to about 25% w/v.

The dissolution can be carried out at a temperature ranging from about 20° C. to about 80° C. and preferably at room temperature (a temperature ranging from about 25° C. to about 30° C.). After the dissolution of aprepitant in the solvent, the solution may optionally be filtered in order to remove any extraneous matter present in the solution using any standard filtration techniques known in the art. If desired, a filtering aid such as celite can be added to the solution.

In step (b) of the process of the present invention, the solvent is substantially removed to provide amorphous aprepitant. The solvent may be removed by, for example, substantially complete evaporation of the solvent, concentrating the solution, cooling to obtain amorphous form and filtering the solid under an inert atmosphere, e.g., a nitrogen atmosphere. Evaporation may be achieved by techniques known in the ark e.g., by lyophilization at about sub-zero temperatures or freeze-drying techniques. The solution may also be completely evaporated in, for example, a pilot plant Rota vapor, a Vacuum Paddle Dryer or in a conventional reactor under vacuum above about 720 mm Hg by flash evaporation techniques by using an agitated thin-film dryer ("ATFD"), or evaporated by spray drying to obtain a dry amorphous powder.

In a preferred embodiment of the present invention, removal of the solvent is carried out by spray-drying. This process includes at least loading a solution containing aprepitant and solvent capable of dissolving aprepitant into a spray drier and spraying the solution at a flow rate ranging from about 10 to about 300 ml/hour, and preferably from about 40 to about 200 ml/hour to recover amorphous aprepitant. The air inlet temperature to the spray drier may range from about 25° C. to about 150° C. and preferably from about 60° C. to 110° C. The outlet air temperature used may range from about 30° C. to about 90° C.

In another embodiment of the present invention, substantial removal of the solvent can be carried out via vertical agitated thin-film drying (ATFD) or evaporation. Agitated thin-film evaporation technology involves separating the volatile component using indirect heat transfer coupled with mechanical agitation of the flowing film under controlled conditions. In ATFD, the starting solution is fed from the top into a cylindrical space between a centered rotary agitator and an outside heating jacket. The rotor rotation agitates the downside-flowing solution while the heating jacket heats it.

If desired, amorphous aprepitant obtained by the above processes may be further dried in, for example, a Vacuum Tray Dryer, Rotocon Vacuum Dryer, Vacuum Paddle Dryer or pilot plant Rota vapor, to further lower residual solvents.

Another aspect of the present invention provides polymorphic mixtures containing polymorph Forms I and II of aprepitant. Aprepitant may be crystallized as a mixture of polymorph Forms I and II in such a way that the ratio between the polymorph is relatively consistent. A polymorphic mixture of the present invention can contain at least about 5 weight %, based on the total weight of the mixture, of polymorph Forms I or II of aprepitant, with the remaining amount of the mixture being the other polymorph form of aprepitant.

In one embodiment of the present invention, a polymorphic mixture can contain about 5 weight % to about 75 weight % of polymorph Form I of aprepitant and about 95 weight % to about 25 weight % of polymorph Form II of aprepitant.

In one embodiment of the present invention, a polymorphic mixture can contain about 11 weight % (±5%) of polymorph Form I of aprepitant and about 89 weight % (±5%) of polymorph Form II of aprepitant.

In still yet another embodiment of the present invention, a polymorphic mixture can contain about 20 weight % (±5%) of polymorph Form I of aprepitant and about 80 weight % (±5%) of polymorph Form II of aprepitant.

In yet another embodiment of the present invention, a polymorphic mixture can contain about 30 weight % (+5%) of polymorph Form I of aprepitant and about 70 weight % (±5%) of polymorph Form II of aprepitant.

In yet another embodiment of the present invention, a polymorphic mixture can contain about 65 weight % (±5%) polymorph Form I of aprepitant and about 35 weight % (±5%) of polymorph Form II of aprepitant.

The polymorphic mixtures of the present invention can be obtained at least (a) providing a solution of aprepitant in one or more solvents capable of dissolving the aprepitant; (b) optionally charcoalizing the solution; (c) optionally filtering the solvent solution to remove any extraneous matter; (d) adding an anti-solvent to the solution; and (e) isolating the polymorphic mixture of aprepitant.

In step (a) of the process of the present invention, a solution is provided by either dissolving aprepitant in a suitable solvent or employing an existing solution of aprepitant from a previous processing step. The starting material used for the processes of the present invention may be any crystalline or other form of aprepitant, including various solvates and hydrates. With crystallization processes, the crystalline form of the starting material generally does not usually affect the final result since the original crystalline form will change once in solution.

Suitable solvents include, but not limited to, alcoholic solvents having from 1 to 6 carbon atoms, aromatic hydrocarbon solvents, non-aromatic hydrocarbon solvents, water, and the like and mixtures thereof. Useful alcoholic solvents include, but are not limited to, methanol, ethanol, propanol, and the like and mixtures thereof. Useful aromatic hydrocarbon solvents include, but are not limited to, benzene, toluene, xylene and the like and mixtures thereof. Useful non-aromatic hydrocarbon solvents include, but are not limited to, hexane, heptane and the like and mixtures thereof. Preferably, the solvent is an alcohol or a mixture of an alcohol with water, and most preferably a mixture of methanol and water. The dissolution can be carried out at a temperature ranging from about 20° C. to about 80° C. The amount of solvent can range from about 10 to about 35% w/v and preferably from about 15 to about 25% w/v.

In steps (b) and (c) of the process of the present invention, the clear solution may be charcoalized and/or filtered to remove any extraneous matter present in the solution using any standard filtration techniques known in the art.

In step (d) of the process of the present invention, an anti-solvent is added to the solution. Suitable anti-solvents include, but are not limited to, water, alkanes, ethers, aromatic hydrocarbons and mixtures thereof. A preferred anti-solvent can be water, butyl ether, isopropyl ether, toluene and p-xylene. The amount of anti-solvent can range from about 0.2 to about 2% w/v and preferably from about 0.5 to about 1% w/v. The anti-solvent can be added at room temperature for a period of about 10 to about 30 minutes In step (e) of the process of the present invention, the polymorphic mixture is isolated from the solution. The polymorphic mixture can be isolated by techniques known in the art, e.g., filtration, evaporation, etc. The isolated Mixtures can then be further dried.

To quantify individual polymorph ratios of initially known Forms I and II of aprepitant, mixtures of these forms were prepared and subjected to powder X-ray diffraction. Plots of individual polymorph percentage vs. peak area corresponding to the individual polymorph were plotted to obtain a linear regression co-efficient. The diffraction of X-rays at approximately 15.3° (2θ) and 18.2° (2θ) corresponding to Forms I and II of aprepitant, respectively, were used to quantify the ratio of polymorphs. Then, to obtain a ratio of polymorphs, the Log of ratio of peak areas of individual polymorphs vs. ratio of polymorphs (by weight) were plotted to obtain a linear regression co-efficient Using the equation, obtained from the linear plot, percentage of individual forms in binary, polymorph mixtures are calculated, initially having the ratio of peak areas and is within the purview of one skilled in the art.

In another aspect of the present invention, the polymorphic mixture of the present invention can be obtained having a purity of equal to or greater than about 98% as measure by HPLC, preferably equal to or greater than about 99%, and more preferably equal to or greater than about 99.5%.

Another aspect of the present invention is directed to a pharmaceutical composition containing the novel amorphous aprepitant and/or polymorphic mixtures of aprepitant in polymorph Forms I and II disclosed herein. Such pharmaceutical compositions may be administered to a mammalian patient in any dosage form, e.g., liquid, powder, elixir, injectable solution, etc. Dosage forms may be adapted for administration to the patient by oral, buccal, parenteral, ophthalmic, rectal, transdermal routes and the like. Oral dosage forms include, but are not limited to, tablets, pills, capsules, troches, sachets, suspensions, powders, lozenges, elixirs and the like. The amorphous aprepitant and/or polymorphic mixtures of aprepitant disclosed herein also may be administered as suppositories, ointments and suspensions, and parenteral suspensions, which are administered by other routes. However, all modes of administrations are contemplated, e.g., orally, rectally, parenterally, intranasally and topically. The most preferred route of administration of the novel amorphous aprepitant and/or polymorphic mixtures of aprepitant disclosed herein is oral. The dosage forms may contain the novel amorphous aprepitant and/or various polymorphic mixtures of aprepitant disclosed herein as is or, alternatively, may contain one or more of the amorphous aprepitant and/or polymorphic mixtures of aprepitant disclosed herein as part of a composition. The pharmaceutical compositions may further contain one or more pharmaceutically acceptable excipients. Suitable excipients and the amounts to use may be readily determined by the formulation scientist based upon experience and consideration of standard procedures and reference works in the field, e.g., the buffering agents, sweetening agents, binders, diluents, fillers, lubricants, wetting agents and disintegrants described hereinabove.

Capsule dosages will contain the novel amorphous aprepitant and/or polymorphic mixtures of aprepitant disclosed herein within a capsule which may be coated with gelatin. Tablets and powders may also be coated with an enteric coating. The enteric-coated powder forms may have coatings containing at least phthalic acid cellulose acetate, hydroxypropylmethyl cellulose phthalate, polyvinyl alcohol phthalate, carboxy methyl ethyl cellulose, a copolymer of styrene and maleic acid, a copolymer of methacrylic acid and methyl methacrylate, and like materials, and if desired, they may be employed with suitable plasticizers and/or extending agents. A coated capsule or tablet may have a coating on the surface thereof or may be a capsule or tablet comprising a powder or granules with an enteric-coating.

Tableting compositions may have few or many components depending upon the tableting method used, the release rate desired and other factors. For example, the compositions of the present invention may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents such calcium carbonate and calcium diphosphate and other diluents known to one of ordinary skill in the art. Yet other suitable diluents include waxes, sugars (e.g., lactose) and sugar alcohols like mannitol and sorbitol, acrylate polymers and copolymers, as well as pectin, dextrin and gelatin.

Other excipients contemplated by the present invention include binders, such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants like magnesium and calcium stearate and sodium stearyl fumarate; flavorings; sweeteners; preservatives; pharmaceutically acceptable dyes and glidants such as silicon dioxide.

Actual dosage levels of the novel amorphous aprepitant and/or polymorphic mixtures of aprepitant disclosed herein may be varied to obtain an amount of the amorphous aprepitant and/or polymorphic mixtures of aprepitant of the present invention that is effective to obtain a desired therapeutic response for a particular composition and method of administration. The selected dosage level therefore depends upon such factors as, for example, the desired therapeutic effect, the route of administration, the desired duration of treatment, and other factors. The total daily dose of the compounds of this invention administered to a host in single or divided dose and can vary widely depending upon a variety of factors including, for example, the body weight, general health, sex, diet, time and route of administration, rates of absorption and excretion, combination with other drugs, the severity of the particular condition being treated, etc. It is believed that the dosage amounts of the amorphous aprepitant and/or polymorphic mixtures of aprepitant disclosed herein can be similar to the dosage amounts of aprepitant sold under the trade name Emend®, e.g., 40 mg, 80 mg and 125 mg/day. The pharmaceutical compositions herein can be formulated in any release form, e.g., immediate release, sustained release, controlled release, etc.

Another embodiment of the present invention provides the novel amorphous aprepitant and/or polymorphic mixtures of aprepitant disclosed herein as a micronized amorphous aprepitant and/or micronized polymorphic mixture of aprepitant having a particle size of less than about 300 microns ($D_{50}$ and/or $D_{90}$), preferably less than about 200 microns, more preferably less than about 150 microns, still more preferably less than about 50 microns, and most preferably less than about 10 microns. The particle size can be determined by such techniques as, for example, Malvern light scattering, a laser light scattering technique, etc., using, e.g., a Malvern Mastersizer 2000. It is noted the notation $D_x$ means that X % of the particles have a diameter less than a specified diameter D. Thus, a $D_{50}$ of about 300 microns means that 50% of the particles of amorphous aprepitant have a diameter less than about 300 microns. The particle sizes of micronized amorphous aprepitant and/or polymorphic mixtures of aprepitant disclosed herein can be obtained by, for example, any milling, grinding, micronizing or other particle size reduction method known in the art to bring the solid state aprepitant into any of the foregoing desired particle size range.

The following examples are provided to enable one skilled in the art to practice the invention and are merely illustrative of the invention. The examples should not be read as limiting the scope of the invention as defined in the features and advantages.

EXPERIMENTAL

The purity was measured by high performance liquid chromatography (HPLC) under the following conditions:

Column: XTerra RP-18, 250 × 4.6 mm, 5μ
Moving phase: % A = Buffer (0.1% O-phosphoric acid in water)
% B = Acetonitrile
Gradient:

| Time(min) | % A | % B |
|---|---|---|
| 0.01 | 58 | 42 |
| 25 | 58 | 42 |
| 45 | 30 | 70 |
| 50 | 30 | 70 |
| 55 | 58 | 42 |
| 65 | 58 | 42 |
| 65 | 58 | 42 |

Detector: UV, 210 nm
Flow rate: 1 ml/min.
Retention time: 19.8 minutes

Characterization

The X-Ray powder diffraction spectrum was measured by an X-ray powder Diffractometer equipped with a Cu-anode (λ=1.5406 Angstrom), X-ray source operated at 45 kV, 40 mA and a Ni filter is used to strip K-beta radiation. Two-theta calibration is performed using an NIST SRM 640c Si standard. The sample was analyzed using the following instrument parameters: measuring range=2-50° 2θ; step width=0.017°; and measuring time per step=1000 sec.

The IR spectrum was obtained on a Perkin Elmer FT-IR spectrometer. The sample was prepared by KBr powder technique registering the spectrum on reflectance.

Example 1

Preparation of Amorphous Aprepitant

Aprepitant (5 g) was dissolved in methanol (500 ml) with stirring at a temperature ranging from about 25° C. to about 45° C. for about 5 to about 15 minutes. The resulting solution was spray-dried to remove the solvent under the following conditions: flow rate 70-200 ml/hr, air inlet temperature between 50-80° C. and outlet temperature between 31-40° C. to provide amorphous aprepitant. Yield—1.7 grams. HPLC purity—99.61%. The XRD and IR patterns of the amorphous aprepitant of this example are set forth in FIGS. 1 and 2, respectively.

Example 2

Preparation of a polymorphic mixture having 11 weight % (+5%) of polymorph Form I of aprepitant and 89 weight % (+5%) of polymorph Form II of aprepitant.

Figure 3:
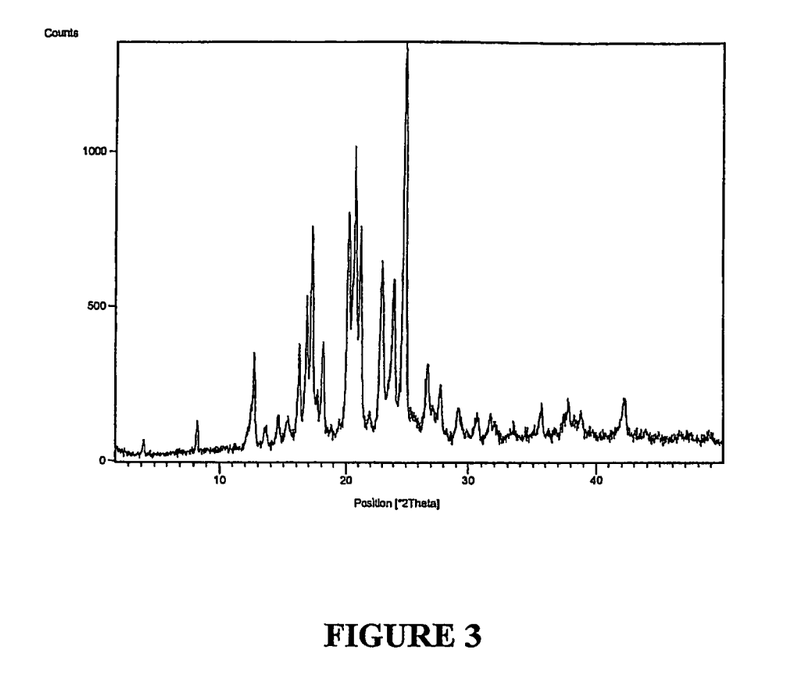
FIG. 3 is a characteristic powder XRD pattern of a polymorphic mixture of about 11 weight % of polymorph Form I of aprepitant and about 89 weight % of polymorph Form II of aprepitant.

Aprepitant (2 g) was dissolved in methanol (20 ml) and heated at temperature ranging from about 50° C. to about 64° C. until complete dissolution. Neutral grade Norit charcoal was added to the solution. The resulting solution was filtered through a hyflo and washed with hot methanol (5 ml). The reaction mixture was cooled down to room temperature, which was then followed by drop wise addition of water (10.5 ml) over about ten to about thirty minutes. After the complete addition of the water, the reaction mixture was stirred at room temperature for 2 hours maintaining the stirrer at 155 rotations per minute (RPM). The resulting solid was filtered under vacuum and allowed to dry overnight. Yield—39 grams. HPLC purity—99.8%. The final product had a XRD pattern as set forth in FIG. 3.

Example 3

Preparation of a polymorphic mixture having 20 weight % (+5%) of polymorph Form I of aprepitant and 80 weight % (+5%) of polymorph Form II of aprepitant.

Figure 4:
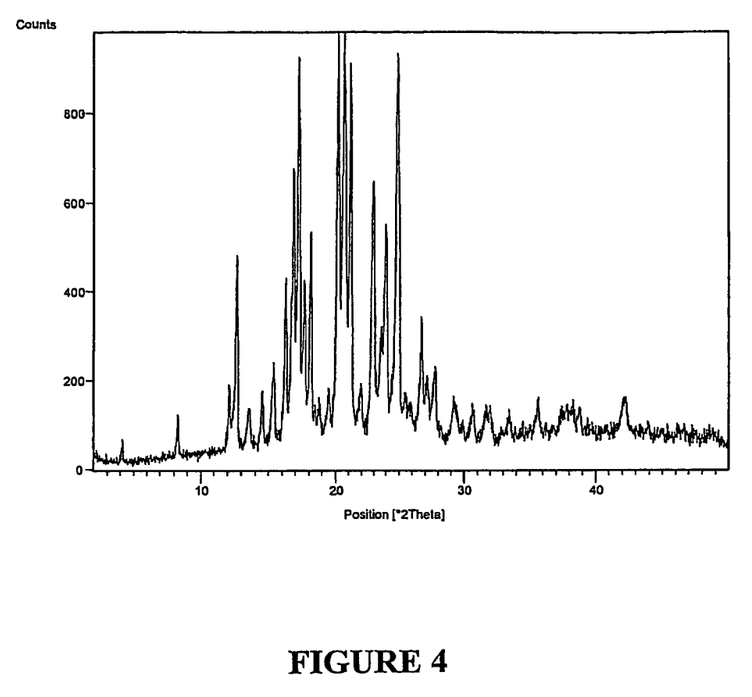
FIG. 4 is a characteristic powder XRD pattern of a polymorphic mixture of about 20 weight % of polymorph Form I of aprepitant and about 80 weight % of polymorph Form II of aprepitant.

Aprepitant (2 g) was dissolved in methanol (20 ml) and heated at temperature ranging from about 50° C. to about 64° C. until complete dissolution. Neutral grade Norit charcoal was added to the solution. The resulting solution was filtered through a hyflo and washed with hot methanol (5 ml). The reaction mixture was cooled down to room temperature, which was then followed by drop wise addition of water (10.5 ml) over about ten to about thirty minutes. After the complete addition of the water, the reaction mixture was stirred at room temperature for 2 hours maintaining the stirrer at 68 RPM. The resulting solid was filtered under vacuum and allowed to dry overnight to obtain a white crystalline powder. Yield—39 grams. HPLC purity—99.8%. The final product had a XRD pattern as set forth in FIG. 4.

Example 4

Preparation of a polymorphic mixture having 30 weight % (+5%) of polymorph Form I of aprepitant and 70 weight % (+5%) of polymorph Form II of aprepitant.

Figure 5:
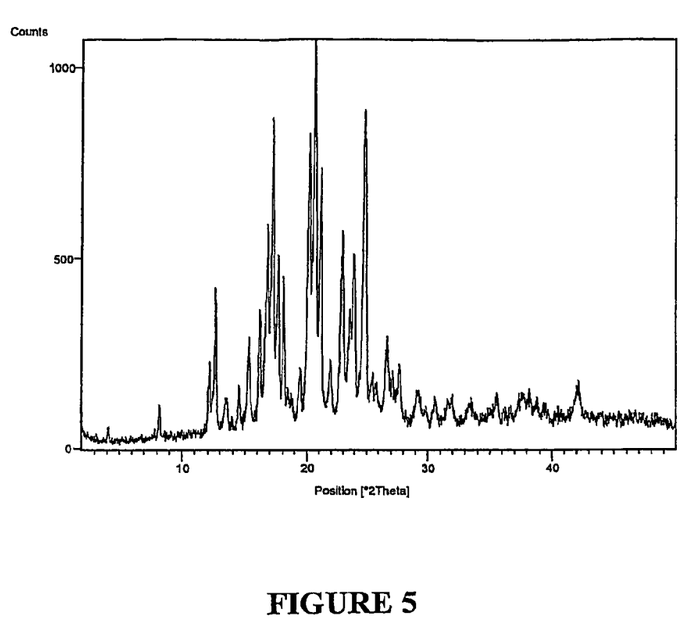
FIG. 5 is a characteristic powder XRD pattern of a polymorphic mixture of about 30 weight % of polymorph Form I of aprepitant and about 70 weight % of polymorph Form II of aprepitant.

Aprepitant (2 g) was dissolved in methanol (20 ml) and heated at temperature ranging from about 50° C. to about 64° C. until complete dissolution. Neutral grade Norit charcoal was added to the solution. The resulting solution was filtered through a hyflo and washed with hot methanol (5 ml). The reaction mixture was cooled down to room temperature, which was then followed by drop wise addition of water (10.5 ml) over about ten to about thirty minutes. After the complete addition of the water, the reaction mixture was stirred at room temperature for 2 hours maintaining the stirrer at 88 RPM. The resulting solid was filtered under vacuum and allowed to dry overnight to obtain a white crystalline powder. Yield—39 grams. HPLC purity—99.8%. The final product had a XRD pattern as set forth in FIG. 5.

Example 5

Preparation of a polymorphic mixture having 69 weight % (+5%) of polymorph Form I of aprepitant and 31 weight % (+5%) of polymorph Form II of aprepitant.

Figure 6:
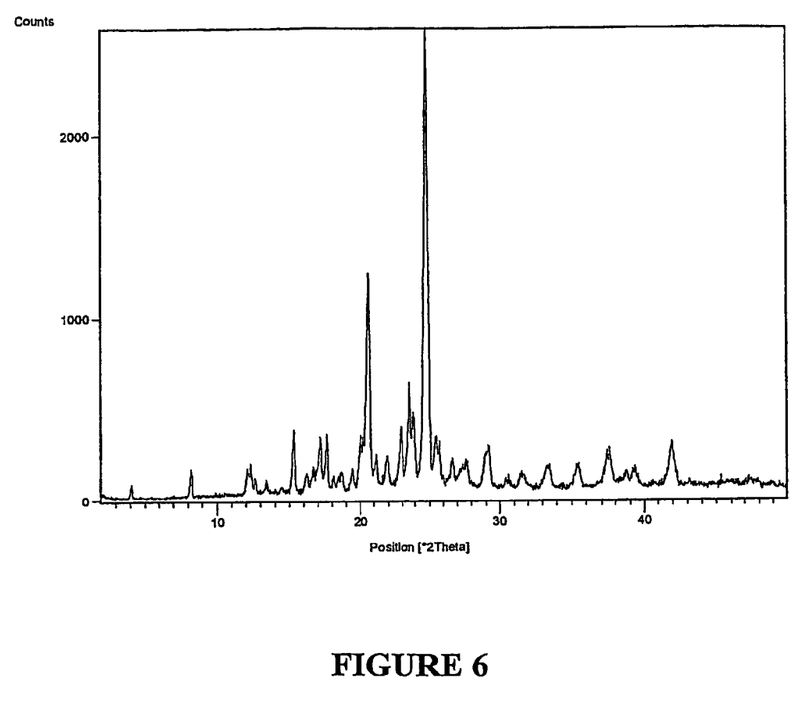
FIG. 6 is a characteristic powder XRD pattern of a polymorphic mixture of about 69 weight % of polymorph Form I of aprepitant and about 31 weight % of polymorph Form II of aprepitant.

Aprepitant (65 g) was dissolved in 650 ml methanol and heated at a temperature from 50° C. to 64° C. until complete dissolution, which was then followed by addition of neutral grade Norit charcoal. The resulting solution was filtered through hyflo and washed with 162.5 ml hot methanol. The reaction mixture was cooled to room temperature, and followed by drop wise addition of 341.2 ml of water for 10 to 30 minutes. The reaction mixture was stirred after the complete addition of water at room temperature for 2 hours maintaining the stirrer at 88-90 RPM. The resulting solid was filtered under vacuum and allowed to dry overnight. Yield—39 grams. HPLC purity—99.8%. The final product had a XRD pattern as set forth in FIG. 6.

Example 6

Preparation of a polymorphic mixture having 63 weight % (±5%) of polymorph Form I of aprepitant and 37 weight % (±5%) of polymorph Form H of aprepitant.

Figure 7:
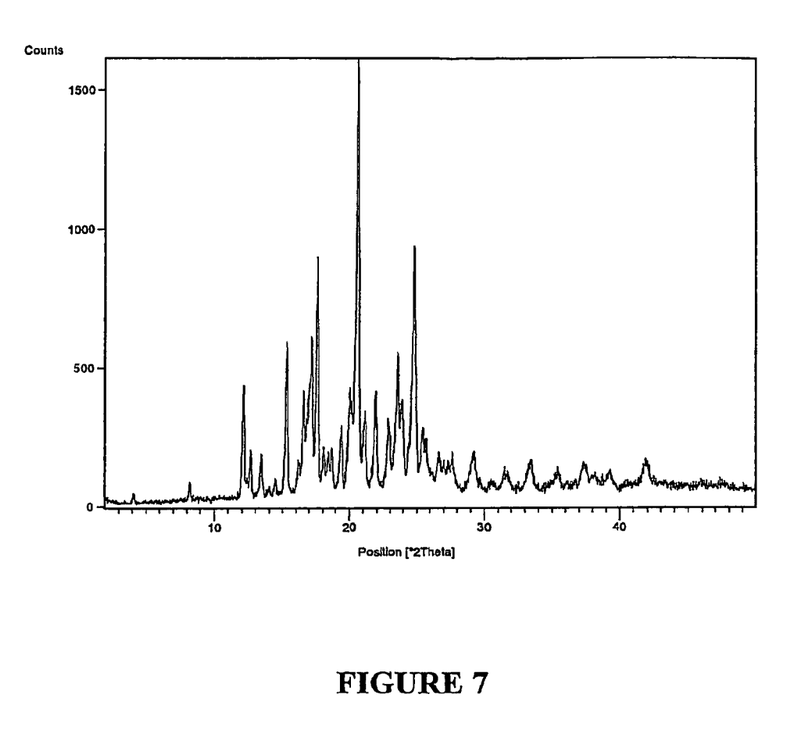
FIG. 7 is a characteristic powder XRD pattern of a polymorphic mixture of about 63 weight % of polymorph Form I of aprepitant and about 37 weight % of polymorph Form II of aprepitant.

Aprepitant (62 g) was dissolved in 620 ml methanol and heated at a temperature from 50° C. to 64° C. until complete dissolution, which was then followed by addition of neutral grade Norit charcoal. The resulting solution was filtered through a hyflo and washed with 155 ml hot methanol. The reaction mixture was cooled to room temperature, and followed by drop wise addition of 325.5 ml of water for 10 to 30 minutes. The reaction mixture was stirred after the complete addition of water at room temperature for 2 hours maintaining the stirrer at 90-92 RPM. The resulting solid was filtered under vacuum and allowed to dry overnight. Yield—39 grams. HPLC purity—99.8%. The final product had a XRD pattern as set forth in FIG. 7.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A crystallization polymorphic mixture, comprising at least about 5 weight %, based on the total weight of the mixture, of polymorph Form I or Form II of aprepitant, with the remaining amount of the mixture being the other polymorph form of aprepitant, wherein the crystallization polymorphic mixture has a $D_{90}$ particle size of less than about 50 microns.

2. The polymorphic mixture of claim 1, comprising about 5 weight % to about 75 weight % of polymorph Form I of aprepitant and about 95 weight % to about 25 weight % of polymorph Form II of aprepitant.

3. The polymorphic mixture of claim 1, comprising about 20 weight % (±5%) of polymorph Form I of aprepitant and about 80 weight % (±5%) of polymorph Form II of aprepitant.

4. The polymorphic mixture of claim 1, comprising about 65 weight % (±5%) of polymorph Form I of aprepitant and about 35 weight % (±5%) of polymorph Form II of aprepitant.

5. The polymorphic mixture of claim 1, comprising about 69 weight % of polymorphic Form I of aprepitant and about 31 weight % of polymorphic Form II of aprepitant.

6. The polymorphic mixture of claim 1, comprising about 63 weight % of polymorphic Form I of aprepitant and about 37 weight % of polymorphic Form II of aprepitant.

7. A pharmaceutical composition comprising a therapeutically effective amount of the crystallization polymorphic mixture according to claim 1 and one or more pharmaceutically acceptable carriers, excipients, diluents or adjuvants.

8. A process for the preparation of a crystallization polymorphic mixture of polymorphic Forms I and II of aprepitant of claim 1, the process comprising:
 (a) providing a solution of aprepitant in one or more solvents capable of dissolving the aprepitant;
 (b) adding an anti-solvent to the solution; and
 (c) isolating the polymorphic mixture.

9. The process of claim 8, wherein the solvent is an alcohol or a mixture of an alcohol and water and the anti-solvent is selected from the group consisting of water, alkane solvent, ether solvent, aromatic hydrocarbon solvent and mixtures thereof.

10. The process of claim 8, wherein the solvent is methanol and the anti-solvent is water.

11. A pharmaceutical composition comprising a therapeutically effective amount of the amorphous aprepitant and the crystallization polymorphic mixture of Form I and Form II of claim 1.

12. A pharmaceutical composition comprising a therapeutically effective amount of the crystallization polymorphic mixture according to claim 2 and one or more pharmaceutically acceptable excipients.

13. The pharmaceutical composition of claim 7, wherein the pharmaceutical composition is in the form of a capsule.

* * * * *